US011160821B2

(12) United States Patent
Lisanti et al.

(10) Patent No.: US 11,160,821 B2
(45) Date of Patent: Nov. 2, 2021

(54) ANTIMITOSCINS: TARGETED INHIBITORS OF MITOCHONDRIAL BIOGENESIS FOR ERADICATING CANCER STEM CELLS

(71) Applicant: LUNELLA BIOTECH, INC., Ontario (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 16/614,623

(22) PCT Filed: May 18, 2018

(86) PCT No.: PCT/US2018/033466
§ 371 (c)(1),
(2) Date: Nov. 18, 2019

(87) PCT Pub. No.: WO2018/213751
PCT Pub. Date: Nov. 22, 2018

(65) Prior Publication Data
US 2020/0179424 A1 Jun. 11, 2020

Related U.S. Application Data

(60) Provisional application No. 62/508,702, filed on May 19, 2017.

(51) Int. Cl.
| A61K 31/7048 | (2006.01) |
| A61K 31/122 | (2006.01) |
| A61K 31/165 | (2006.01) |
| A61K 31/47 | (2006.01) |
| A61K 47/54 | (2017.01) |
| A61K 31/4709 | (2006.01) |

(52) U.S. Cl.
CPC ........ *A61K 31/7048* (2013.01); *A61K 31/122* (2013.01); *A61K 31/165* (2013.01); *A61K 31/47* (2013.01); *A61K 31/4709* (2013.01); *A61K 47/54* (2017.08); *A61K 47/542* (2017.08); *A61K 47/548* (2017.08)

(58) Field of Classification Search
CPC .............. A61K 31/7048; A61K 47/542; A61K 47/548; A61K 31/47; A61K 31/165; A61K 31/4709; A61K 31/122; A61K 47/54
USPC ........................................................ 514/29
See application file for complete search history.

(56) References Cited

U.S. PATENT DOCUMENTS

| 3,517,067 A | 6/1970 | Stern |
| 4,599,326 A | 7/1986 | Marvola et al. |
| 5,168,057 A | 12/1992 | Oh et al. |
| 5,250,518 A | 10/1993 | Kobrehel et al. |
| 5,441,939 A | 8/1995 | Yang |
| 5,795,871 A | 8/1998 | Narita et al. |
| 5,837,696 A | 11/1998 | Golub et al. |
| 6,043,226 A | 3/2000 | Lundy et al. |
| 6,165,999 A | 12/2000 | Vu |
| 6,475,518 B1 | 11/2002 | Baumgart et al. |
| 6,858,598 B1 | 2/2005 | McKearn et al. |
| 7,405,227 B2 | 7/2008 | Kun et al. |
| 7,485,298 B2 | 2/2009 | Powell |
| 8,075,902 B2 | 12/2011 | Powell |
| 8,357,723 B2 | 1/2013 | Satyam |
| 8,741,853 B2 | 6/2014 | Steliou |
| 9,394,233 B2 | 7/2016 | Merino et al. |
| 9,622,982 B2 | 4/2017 | Bannister et al. |
| 9,675,578 B2 | 6/2017 | Desai et al. |
| 9,801,922 B2 | 10/2017 | Spitz et al. |
| 10,188,668 B2 | 1/2019 | Bannister et al. |
| 2001/0002404 A1 | 5/2001 | Webb |
| 2004/0161405 A9 | 8/2004 | Rothbard et al. |
| 2005/0002942 A1 | 1/2005 | Vlahov et al. |
| 2005/0209292 A1 | 9/2005 | Chuang et al. |
| 2005/0256081 A1 | 11/2005 | Peyman |
| 2007/0048296 A1 | 3/2007 | Kajander et al. |
| 2007/0105937 A1 | 5/2007 | Pappolla et al. |
| 2008/0045589 A1 | 2/2008 | Kelley |
| 2008/0118432 A1 | 5/2008 | Bergstein et al. |
| 2008/0160007 A1 | 7/2008 | Powell |

(Continued)

FOREIGN PATENT DOCUMENTS

| CN | 1 706 391 | 12/2005 |
| CN | 1 837 225 | 9/2006 |
| CN | 1 837 229 | 9/2006 |
| CN | 103536530 A | 1/2014 |
| CN | 104352566 | 2/2015 |
| CN | 105884633 A | 8/2016 |
| CN | 106 511 317 | 3/2017 |
| EP | 0656422 | 6/1995 |
| EP | 0941998 | 9/2004 |

(Continued)

OTHER PUBLICATIONS

Barden et al. "Glycylcyclines". 3. 9-Aminodoxycyclinecarboxamides. J. Med. Chem. 1994, 37, 3205-3211. (Year: 1994).*

(Continued)

*Primary Examiner* — Yih-Horng Shiao
(74) *Attorney, Agent, or Firm* — Nixon & Vanderhye, P.C.

(57) ABSTRACT

Antibiotics having intrinsic anti-mitochondrial properties may be chemically modified to target the antibiotics to mitochondria, and the resulting "antimitoscins" may have enhanced anti-cancer properties, among other advantageous properties. Also described are methods for identifying antimitoscins, methods of using antimitoscins to target cancer stem cells, and pharmaceutical compositions for treating cancer containing one or more antimitoscins as the active ingredient. Specific antimitoscins compounds and groups of antimitoscins are also disclosed.

6 Claims, 8 Drawing Sheets

(56) References Cited

U.S. PATENT DOCUMENTS

| | | |
|---|---|---|
| 2008/0241959 A1 | 10/2008 | Culic et al. |
| 2009/0099062 A1 | 4/2009 | Lee et al. |
| 2009/0099080 A1 | 4/2009 | Altieri et al. |
| 2009/0311249 A1 | 12/2009 | Gianni et al. |
| 2010/0120679 A1 | 5/2010 | Xu et al. |
| 2010/0202969 A1 | 8/2010 | Panyam et al. |
| 2010/0285001 A1 | 11/2010 | Land et al. |
| 2011/0268722 A1 | 11/2011 | Siegelin et al. |
| 2012/0141467 A1 | 6/2012 | Schneider |
| 2014/0038886 A1 | 2/2014 | Mier et al. |
| 2014/0142056 A1 | 5/2014 | Shanmugam et al. |
| 2014/0187611 A1 | 7/2014 | Auwerx et al. |
| 2014/0303085 A1 | 10/2014 | Wong et al. |
| 2014/0364595 A1 | 11/2014 | Bapat et al. |
| 2015/0079154 A1 | 3/2015 | Zender et al. |
| 2015/0224169 A1 | 8/2015 | Bhatia et al. |
| 2015/0224206 A1 | 8/2015 | Van |
| 2015/0231069 A1 | 8/2015 | Modi |
| 2016/0008332 A1 | 1/2016 | Haq et al. |
| 2016/0075726 A1 | 3/2016 | Neuzil |
| 2016/0296480 A1 | 10/2016 | Frank et al. |
| 2016/0339106 A1 | 11/2016 | Shanta |
| 2017/0014361 A1 | 1/2017 | Dhar |
| 2017/0035832 A1 | 2/2017 | Liu et al. |
| 2017/0095460 A1 | 4/2017 | Fathi et al. |
| 2017/0224730 A1 | 8/2017 | Berenson |
| 2017/0232008 A1 | 8/2017 | Zeicher |
| 2018/0214472 A1 | 8/2018 | Bapat et al. |

FOREIGN PATENT DOCUMENTS

| | | |
|---|---|---|
| GB | 2472138 | 1/2011 |
| JP | 2016-155679 | 9/2016 |
| RU | 2 223 103 | 2/2004 |
| RU | 2480201 C2 | 4/2013 |
| WO | WO 1992012717 * | 8/1992 |
| WO | 1995015770 | 6/1995 |
| WO | 99/26582 | 6/1999 |
| WO | WO 2008/145116 | 12/2008 |
| WO | 2010/121177 | 10/2010 |
| WO | WO 2011/031474 | 3/2011 |
| WO | WO 2011109899 A1 | 9/2011 |
| WO | WO 2012/177986 A2 | 12/2012 |
| WO | 2013/040206 | 3/2013 |
| WO | 2015/191668 | 12/2015 |
| WO | 2016/027089 | 2/2016 |
| WO | 2016/059247 | 4/2016 |
| WO | 2018/027252 | 2/2018 |
| WO | 2018/136598 | 7/2018 |
| WO | 2018/136617 | 7/2018 |
| WO | 2018/195434 | 10/2018 |
| WO | 2018/195446 | 10/2018 |
| WO | 2018/202910 | 11/2018 |
| WO | 2018/213751 | 11/2018 |
| WO | 2018/213764 | 11/2018 |
| WO | 2018/218242 | 11/2018 |
| WO | WO 2019104115 | 5/2019 |
| WO | WO 2019126179 | 6/2019 |

OTHER PUBLICATIONS

Lamb et al. Antibiotics that target mitochondria effectively eradicate cancer stem cells, across multiple tumor types: Treating cancer like an infectious disease. Oncotarget, vol. 6, No. 7, pp. 4569-4584, 2015. (Year: 2015).*

De Francesco et al. Vitamin C and Doxycycline: A synthetic lethal combination therapy targeting metabolic flexibility in cancer stem cells (CSCs). Oncotarget, 2017, vol. 8, (No. 40), pp. 67269-67286. (Year: 2017).*

DeLuca et al., "Mitochondrial biogenesis is required for the anchorage-independent survival and propagation of stem-like cancer cells", Oncotarget, vol. 6, No. 17, pp. 14777-14795, Jun. 9, 2015.

Zeina et al., "Doxycycline and other Tetracyclines in the Treatement of Bone Metastasis", Anticancer Drugs. Nov. 2003, vol. 14, Issue 10, pp. 773-778. (Abstract Only).

Chen et al., "Mitochondria-targeted Drug Delivery System for Cancer Treatment", Journal of Drug Targeting, 2015, vol. 24, No. 6, pp. 1-11.

Zhang et al., Mitochondria Targeting Nano Agents in Cancer Therapeutics (Review), Oncology Letters, vol. 12, pp. 4887-4890, 2016.

Chile Opposition in Chile Application No. 201903283 date of writing Feb. 7, 2020.

Office Action for Australian Application No. 2018270129 dated Sep. 18, 2020.

Jóźwiak, M. et al. "Anticancer activities of fatty acids and their heterocyclic derivatives" European Journal of Pharmacology vol. 871, Mar. 15, 2020, 172937.

CAS Registry No. 530-43-8; STN Entry Date Nov. 16, 1984; chloramphenicol palmitate.

CAS Registry No. 31450-30-3; STN Entry Date Nov. 16, 1984; 9-Amino-9-deoxoerythromycin palmitate.

Chun-hui Liang et al. "Synthesis of Doxorubicin α-Linolenic Acid Conjugate and Evaluation of Its Antitumor Activity" *Molecular Pharmaceutics* 2014 11 (5), 1378-1390.

Li, S. et al. The targeting mechanism of DHA ligand and its conjugate with Gemcitabine for the enhanced tumor therapy. *Oncotarget*. 2014;5(11):3622-3635.

Giacometti et al., "In-vitro activity of macrolides alone and in combination with artemisin, atovaquone, dapsone, minocycline or pyrimethamine against *Cryptosporidium parvum*", Journal of Antimicrobial Chemotherapy, 1996, vol. 38, pp. 399-408.

M2 Pharma [London], "Study finds vitamin C and antibiotics effectively killed cancer stem cells", Jun. 13, 2017, 2 pages.

Sotgia et al., "A mitochondrial based oncology platform for targeting cancer stem cells (CSCs): MITO-ONC-RX", Journal Cell Cycle, Sep. 26, 2018, vol. 17, No. 17, pp. 2091-2100.

Komatsu et al., "Clarithromycin enhances bortezomib-induced cytotoxicity via endoplasmic reticulum stress-mediated CHOP (GADD153) induction and autophagy in breast cancer cells", International Journal of Oncology, vol. 40, 2012, pp. 1029-1039.

Moriya et al., "Macrolide antibiotics block autophagy flux and sensitize to bortezomib via endoplasmic reticulum stress-mediated CHOP induction in myeloma cells", International Journal of Oncology, vol. 42, 2013, pp. 1541-1550.

Petovari et al., "Targeting cellular metabolism using rapamycin and/or doxycycline enhances anti-tumour effects in human glioma cells", Cancer Cell Int., 18:211, 2018, pp. 1-17.

Van Nuffel et al., "Repurposing Drugs in Oncology (ReDO)—clarithromycin as an anti-cancer agent", ecancermedicalscience, 2015, pp. 1-26.

Jankowitsch et al., "A novel N,N-8-amino-8-demethyl-D-riboflavin dimethyltransferase (RosA) catalyzing the two terminal steps of roseoflavin biosynthesis in *Streptomyces davawensis*", The American Society for Biochemistry and Molecular Biology, Inc., 2011, pp. 1-25.

Murphy, "Targeting lipophilic cations to mitochondria", Biochimica et Biophysica Acta, 2008, pp. 1028-1031.

Ross et al., "Lipophilic Triphenylphosphonium Cations as Tools in Mitochondrial Bioenergetics and Free Radical Biology", Biochemistry (Moscow), vol. 70, No. 2, 2005, pp. 222-230. [Translated from Biokhimiya].

Gonzalez et al., "Mitochondria, Energy and Cancer: The Relationship with Ascorbic Acid", JOM, vol. 25, No. 1, 2010, pp. 29-38.

Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.

Rebecca Lamb, et al., "Antibiotics that target mitochondria effectively eradicate cancer stem cells, across multiple tumor types: Treating cancer like an infectious disease", Oncotarget, Jan. 22, 2015, vol. 6, No. 7, pp. 4569-4584.

(56) References Cited

OTHER PUBLICATIONS

Valter D. Longo, Ph.D., et al., "Calorie restriction and cancer prevention; metabolic and molecular mechanisms", Trends Pharmacol Sci., 89?98, doi: 10.1016/j.tips.2009.11.004, Feb. 2010, vol. 31, No. 2, 19 pages.

"Mitochondrial ribosome", Wikipedia, Feb. 21, 2016, retrieved Sep. 5, 2019, 2 pages, https://en.wikipedia.org/w/index.php?title=Mitochondrial_ribosome&oldid=706108827.

International Search Report for PCT/US2018/033466 dated Sep. 20, 2018, 4 pages.

Written Opinion of the ISA for PCT/US2018/033466 dated Sep. 20, 2018, 4 pages.

IPRP for International Application No. PCT/US2018/062956 dated Apr. 30, 2020.

Russian Search Report for Russian Application No. 2019142102 dated Oct. 30, 2020.

Chhikara, B.S. et al., "Fatty acyl amide derivatives of doxorubicin: Synthesis and in vitro anticancer activities." European Journal of Medicinal Chemistry, 2011, 46(6), pp. 2037-2042. Doi:10.1016/j.ejmech.2011.02.056.

Roberta Censi and Piera Di Martino. "Polymorph Impact on the Bioavailability and Stability of Poorly Soluble Drugs." Molecules 2015, 20, pp. 18759-18776; doi:10.3390/molecules2010018759.

Toxicology and Carcinogenesis studies of erythromycin stearate (CAS No. 643-22-1) in F344/N Rats and B6C3F1 mice. National Toxicology Program, P.O. Box 12233 Research Triangle Park, NC 27709, Dec. 1988. Cm. c.5.

Fiorillo M. et al., Repurposing atovaquone: targeting mitochondrial complex III and OXPHOS to eradicate cancer stem cells. Oncotarget, 2016; 7(23), pp. 34084-34099. Doi: 10.18632/oncotarget.9122.

Zhang L. et al., Doxycycline inhibits the cancer stem cell phenotype and epithelial-to-mesenchymal transition in breast cancer. Cell cycle, Published online Oct. 18, 2016, v. 16, 8, pp. 737-745. Doi:10.1080/15384101.2016.1241929.

Liu Ke, et al., "Measurement of Erythromycin A in Erythromycin Stearate Granules by HPLC", West China J. Pharm Sci, No. 6, vol. 27, pp. 724-725 (Dec. 31, 2012).

Chinese Office Action for Chinese Application No. 2018800466510, dated Jan. 13, 2021 (w/English Translation).

Supplemental European Search Report for EP 18 80 3298 dated Feb. 8, 2021.

Chenevert et al., "Enantioselective hydrolysis of (+/−)—chloramphenicol palmitate by hydrolases", Biorganic & Medicinal Chemistry Letters, Elsevier, Amsterdam, NL, vol. 4, No. 24, Dec. 22, 1994, pp. 2941-2944, XP026646478.

Notice of the Reasons for Refusal for Application No. 2019-563871 dated Mar. 12, 2021 including English Translation.

C. Roumana and G. Velrajb, "Investigation of Molecular Interactions of Myristic Acid with Antibiotic through Viscometric, Acoustic and Refractometric Studies", 2010 Second International Conference on Computer Research and Development, 2010, pp. 623-628, doi: 10.1109/ICCRD.2010.134.

* cited by examiner

Palmitic Acid — Tetracycline Family Member

TPP — Carbon Spacer Arm — Tetracycline Family Member

ANTIMITOSCINS: TARGETED INHIBITORS OF MITOCHONDRIAL BIOGENESIS FOR ERADICATING CANCER STEM CELLS

This application is the U.S. national phase of International Application No. PCT/US2018/033466 filed May 18, 2018 which designated the U.S. and claims priority to U.S. Provisional Patent Application No. 62/508,702 filed May 19, 2017, the entire contents of each of which are hereby incorporated by reference.

FIELD

The present disclosure relates to "antimitoscins," antibiotics having intrinsic anti-mitochondrial properties that are chemically modified to target the antibiotics to mitochondria, and includes methods for synthesizing antimitoscins, methods of using antimitoscins to target cancer stem cells, and pharmaceutical compositions for both treating cancer and reducing drug resistance in cancer cells, the pharmaceutical compositions containing one or more antimitoscins as the active ingredient.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle*, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget*, 5(22):11029-11037 (2014).

Functional inhibition of mitochondrial biogenesis using the off-target effects of certain bacteriostatic antibiotics or OXPHOS inhibitors provides additional evidence that functional mitochondria are required for the propagation of cancer stem cells. The inventors recently showed that a mitochondrial fluorescent dye (MitoTracker) could be effectively used for the enrichment and purification of cancer stem-like cells (CSCs) from a heterogeneous population of living cells. Farnie et al., *Oncotarget*, 6:30272-30486 (2015). Cancer cells with the highest mitochondrial mass had the strongest functional ability to undergo anchorage-independent growth, a characteristic normally associated with metastatic potential. The 'Mito-high' cell sub-population also had the highest tumor-initiating activity in vivo, as shown using pre-clinical models. The inventors also demonstrated that several classes of non-toxic antibiotics could be used to halt CSC propagation. Lamb et al., *Oncotarget*, 6:4569-4584 (2015). Because of the conserved evolutionary similarities between aerobic bacteria and mitochondria, certain classes of antibiotics or compounds having antibiotic activity can inhibit mitochondrial protein translation as an off-target side-effect.

SUMMARY

In view of the foregoing background, it is an object of this disclosure to demonstrate that existing antibiotics having intrinsic anti-mitochondrial properties can be chemically modified to target the mitochondria and thus can be used to eradicate CSCs. Described herein are examples of existing antibiotics having intrinsic anti-mitochondrial properties that have been chemically modified with one or more mitochondria-targeting signals that, as a result, have enhanced anti-cancer properties. The term "antimitoscin" used herein broadly refers to an antibiotic having intrinsic anti-mitochondrial properties that is chemically modified to target the antibiotic to mitochondria. The contemporary art considers intrinsic anti-mitochondrial activity in antibiotics to be an unwanted side-effect. Indeed, some potential antibiotics have been excluded from trials due to excessive anti-mitochondrial properties, and researchers have viewed anti-mitochondrial activity as a potential drawback. However, under the present approach, an antibiotic's intrinsic anti-mitochondrial activity can become the basis for an entirely new therapeutic. The inventors have determined that these anti-mitochondrial properties may be harnessed and enhanced through chemical modification. As a result, antibiotics with intrinsic anti-mitochondrial activity may be re-purposed as novel therapeutics for, among other potential therapies, anti-cancer treatments. These compounds may bind to either the large sub-unit or the small sub-unit of the mitochondrial ribosome (or in some instances, both) and inhibit mitochondrial biogenesis. Alternatively, these compounds may bind to the inner mitochondrial membrane to block the OXPHOS pathway and thus inhibit mitochondrial metabolism. The present disclosure further describes methods of synthesizing antimitoscins, methods of using antimitoscins to target cancer stem cells, and pharmaceutical compositions for both treating cancer and for reducing drug resistance, the pharmaceutical compositions containing one or more antimitoscins as the active ingredient. The present disclosure further describes methods for monitoring the effectiveness of an antimitoscin therapy. The methods may include obtaining a tissue sample from a patent, determining the level of at least one CSC marker in the sample, and classifying the antimitoscin therapy as effective if the sample is determined to have a decreased level of at least one CSC marker relative to a threshold level. The CSC marker may be at least one of CD44, Sox2, Nanog, Oct. 4, MYC, and ALDH.

The present disclosure may, in some embodiments, take the form of an antimitoscin. Exemplar antimitoscins are disclosed herein. In some embodiments, the antimitoscin comprises an antibiotic having intrinsic anti-mitochondrial properties and a mitochondria-targeting compound. In some embodiments, the antibiotic is a member of the tetracycline family, the erthyromycin family, chloramphenicol, pyrvinium pamoate, atovaquone, and bedaquiline. The mitochondria-targeting compound may be a chemical modification to the antibiotic. In some embodiments, the mitochondria-targeting compound is at least one compound selected from the group comprising a membrane targeting signal and a mitochondrial ribosome-targeting signal. In some embodiments, the membrane targeting signal is a compound selected from the group comprising palmitic acid, stearic acid, myristic acid, and oleic acid. In some embodiments, the mitochondrial targeting signal is selected from the group comprising tri-phenyl-phosphonium and guanidinium. In some embodiments, the antimitoscin possesses anti-cancer activity. In some embodiments, the antimitoscin binds to the large sub-unit or the small sub-unit of the mitochondrial ribosome. In some embodiments, the antimitoscin binds to at least one of the large sub-units of the mitochondrial ribosome and the small sub-unit of the mitochondrial ribosome. In some embodiments, the antimitoscin binds to the inner mitochondrial membrane. In some embodiments, an antimitoscin possesses radiosensitizing activity, photosensitizing activity, sensitizes cancer cells to chemotherapeutic agents, sensitizes cancer cells to natural substances, and/or sensitizes cancer cells to caloric restriction. In some embodiments, the present disclosure relates to methods of treating cancer comprising administering to a patient in need thereof of a pharmaceutically effective amount of an antimitoscin and a pharmaceutically acceptable carrier. In some embodiments, the present disclosure relates to a pharmaceutical composition for treating cancer containing, as the active ingredient, at least one antimitoscin. In some embodiments, the pharmaceutical composition comprises a plurality of antimitoscins. Embodiments of the present approach may take the form of methods of synthesizing antimitoscins. Embodiments of the present approach may also take the form of improving the anti-cancer properties of an antibiotic.

The inventors analyzed phenotypic properties of CSCs that could be targeted across a wide range of cancer types, and identified a strict dependence of CSCs on mitochondrial biogenesis for the clonal expansion and survival of a CSC. Previous work by the inventors demonstrated that different classes of FDA-approved antibiotics, and in particular tetracyclines such as doxycycline and erythromycin, have an off-target effect of inhibiting mitochondrial biogenesis. As a result, such compounds have efficacy for eradicating CSCs. However, these common antibiotics were not designed to target the mitochondria, and therefore their anti-cancer efficacy is limited. Under the present approach, existing antibiotics having intrinsic anti-mitochondrial properties may be chemically modified to form antimitoscins, to target the mitochondria, and inhibit mitochondrial biogenesis and metabolism. Antimitoscins selectively inhibit CSCs because mitochondrial biogenesis is upregulated in CSCs and is required for propagation and survival. As a result of their ability to inhibit mitochondrial biogenesis, antimitoscins have enhanced anti-cancer properties.

DESCRIPTION

Figure 1A:
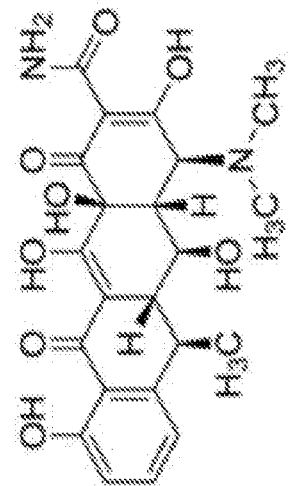
FIG. 1 illustrates members of the tetracycline family, including (A) tetracycline, (B) doxycycline, (C) tigecycline, and (D) minocycline.
Figure 1B:
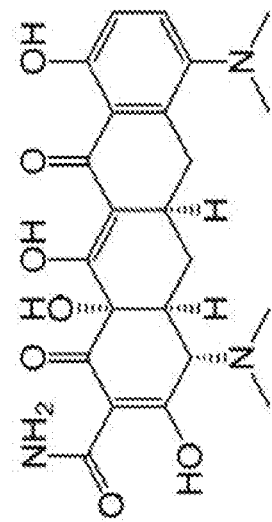
Figure 1C:
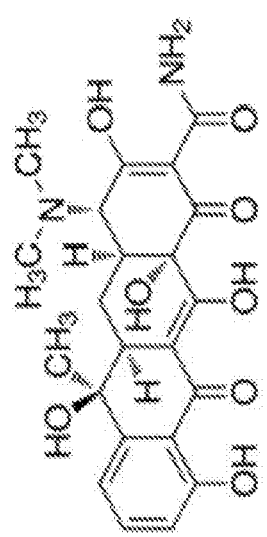
Figure 1D:
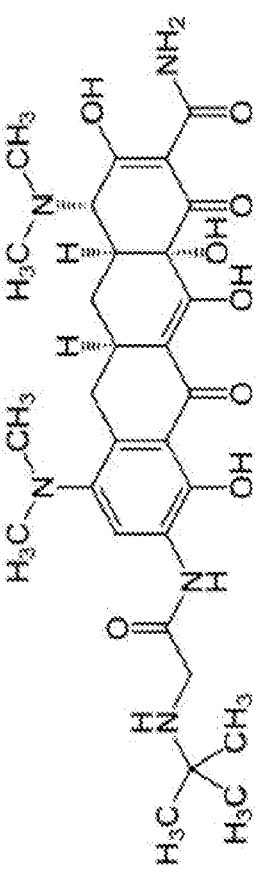

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The mitochondria is an untapped gateway for treating a number of afflictions, ranging from cancer to bacterial and fungal infections to aging. Functional mitochondria are required for the propagation of cancer stem cells. Inhibiting mitochondrial biogenesis and metabolism in cancer cells impedes the propagation of those cells. Mitochondrial inhibitors therefore represent a new class of anti-cancer therapeutics.

As disclosed herein, existing antibiotics having intrinsic anti-mitochondrial properties may be chemically-modified with at least one mitochondria-targeting compound. The mitochondria-targeting compound may be a chemical modification to the antibiotic, and the chemical modification may be made according to chemical synthesis methods as are known in the art. The mitochondria-targeting compound may be one of a membrane-targeting signal and a mitochondrial-ribosome targeting signal. In some embodiments, the antibiotic having intrinsic anti-mitochondrial properties may be chemically-modified with at least one membrane-targeting signal and at least one mitochondrial-targeting signal. The resulting antimitoscin may be used as an anti-cancer therapeutic, as well as to target bacteria and pathogenic yeast, provide anti-aging benefits, function as radiosensitizers and/or photo-sensitizers, and/or sensitize bulk cancer cells and cancer stem cells to chemotherapeutic agents, pharmaceuticals, and/or other natural substances.

Novel antibiotics having intrinsic anti-mitochondrial properties that are chemically modified to target the antibiotics to mitochondria, referred to herein as "antimitoscins," may be formed by the addition of at least one membrane-targeting signal and/or at least one mitochondrial-targeting signal to an antibiotic having intrinsic anti-mitochondrial properties. Such chemical modifications increase the efficiency of the specific targeting of these compounds to the mitochondria and in particular the mitochondrial ribosome. The resulting compound, an antimitoscin, has dramatically enhanced therapeutic properties, including anti-cancer properties.

FIGS. 1-4 provide examples of known antibiotics having intrinsic anti-mitochondrial properties that are chemically modified to target the antibiotics to mitochondria to form an antimitoscin under the present approach. Antibiotics in the tetracycline family are examples of antibiotics having intrinsic anti-mitochondrial properties that are chemically modified to target the antibiotics to mitochondria to form antimitoscins having efficacy as anti-cancer therapeutics. FIG. 1 illustrates members of the tetracycline family, including (A) tetracycline, (B) doxycycline, (C) tigecycline, and (D) minocycline. Each of these broad-spectrum antibiotics may be chemically modified with at least one mitochondrial ribosome-targeting compound to form an antimitoscin. It should be appreciated that the specific antibiotics shown are demonstrative, and that the scope of the present approach is not limited to only those structures shown. For example, other members of the tetracycline family not specifically identified herein may be used as an initial compound for forming an antimitoscin. This may include, as a non-exhaustive list of examples only, chlortetracycline, oxytetracycline, demeclocycline, lymecycline, meclocycline, methacycline, rolitetracycline, chlortetracycline, omadacycline, and sarecycline.

Figure 2B:
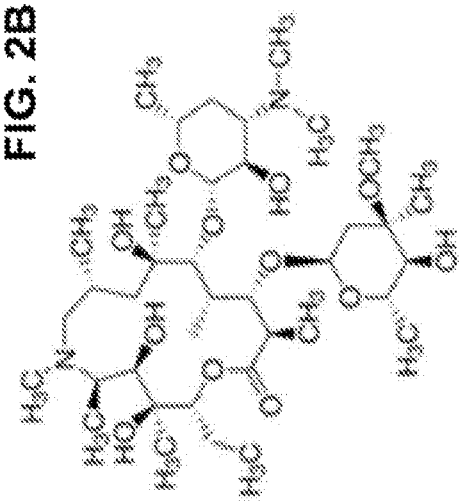
FIG. 2 illustrates members of the erythromycin family, including (A) erythromycin, (B) clarithromycin, and (C) azithromycin.
Figure 2C:
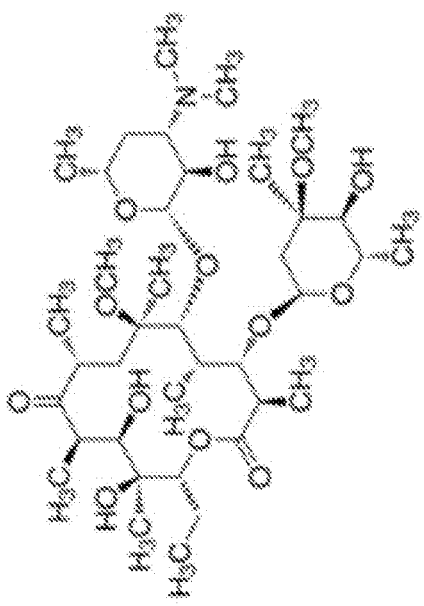
Figure 2A:
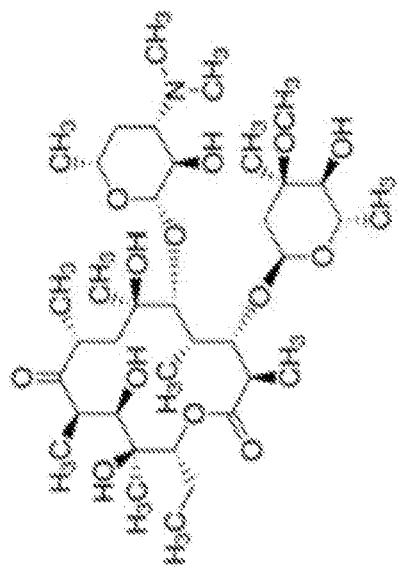

Antibiotics in the erythromycin family are additional examples of antibiotics having intrinsic anti-mitochondrial properties that are chemically modified to target the antibiotics to mitochondria to form antimitoscins having efficacy as anti-cancer therapeutics. FIG. 2 shows the chemical structures for sample erythromycin family members, including (A) erythromycin, (B) azithromycin, and (C) clarithromycin. Each of these antibiotics may be chemically modified with at least one mitochondria-targeting compound to form an antimitoscin. It should be appreciated that the specific antibiotics shown are demonstrative, and that the scope of the present approach is not limited to only those structures shown. For example, other members of the tetracycline family not specifically identified herein may be used as an initial compound for forming an antimitoscin. This may include, for example, chlortetracycline, oxytetracycline, demeclocycline, lymecycline, meclocycline, methacycline, minocycline, rolitetracycline, tigecycline, omadacycline, and sarecycline, to name a few further examples.

Figure 3B:
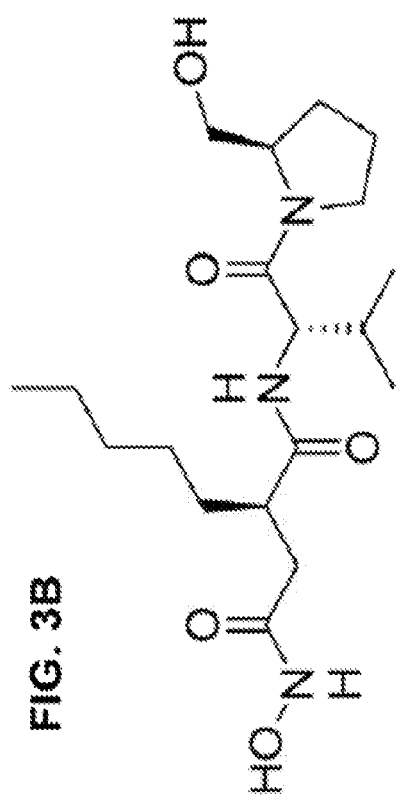
FIG. 3 illustrates other antibiotics known to inhibit the mitochondrial ribosome or mitochondrial protein translation via off-target side-effects, including (A) chloramphenicol, (B) actinonin, and (C) levofloxacin.
Figure 3A:
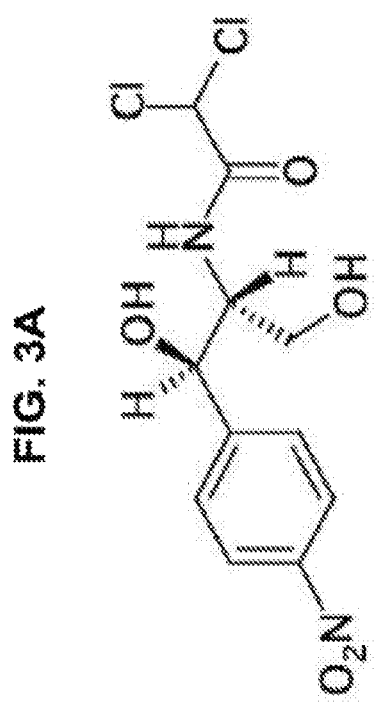
Figure 3C:
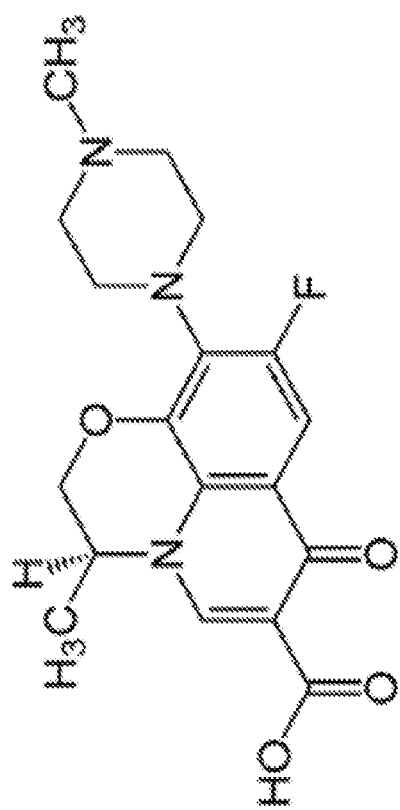
Figure 4A:
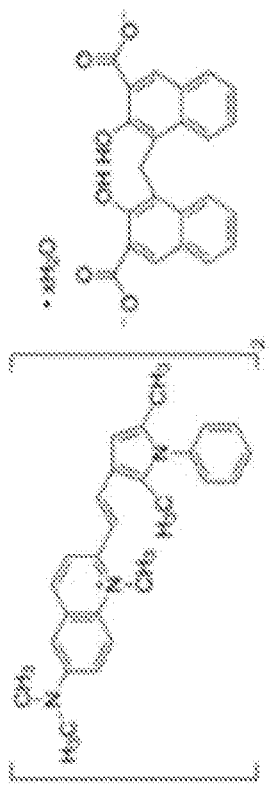
FIG. 4 illustrates other antibiotics known to inhibit the mitochondrial ribosome or mitochondrial protein translation via direct effects on mitochondrial oxygen consumption, including (A) pyrvinium pamoate, (B) atovaquone, and (C) bedaquiline.
Figure 4B:
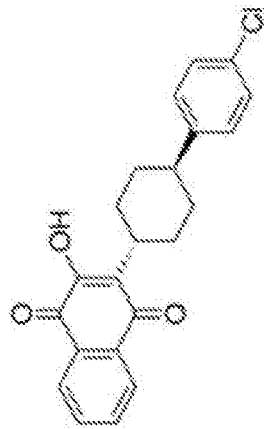
Figure 4C:
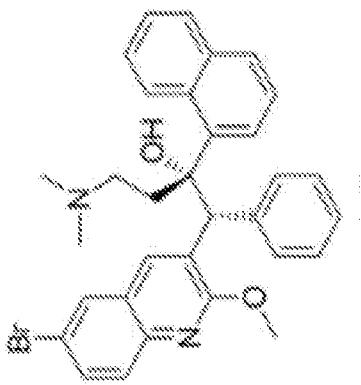
Figure 5A:
FIG. 5 shows the structures of membrane-targeting signals including the fatty acids (A) stearic acid, (B) myristic acid, (C) palmitic acid, and (D) oleic acid.
Figure 5C:
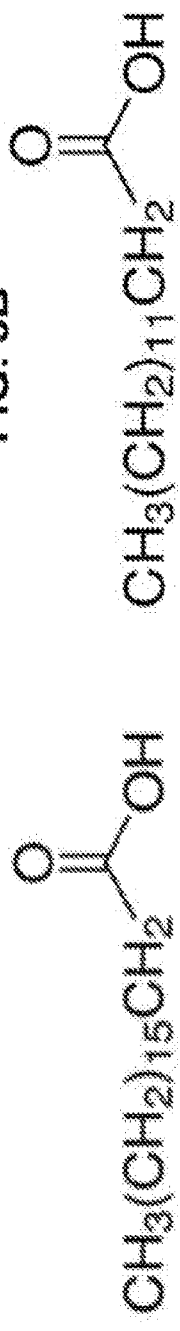
Figure 5B:
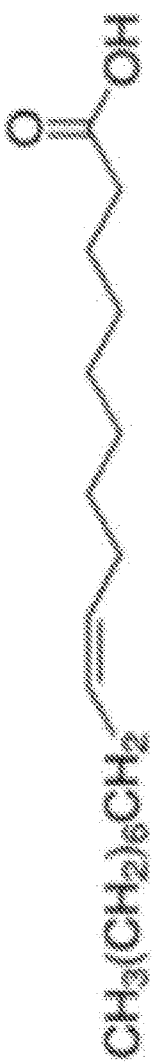
Figure 5D:
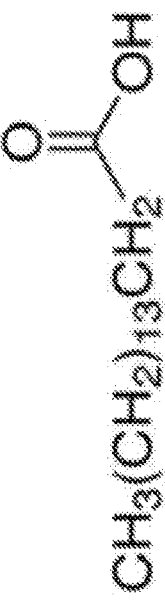

Other known antibiotics having intrinsic anti-mitochondrial properties that are chemically modified to target the antibiotics to mitochondria may be antimitoscins. FIG. 3 shows other antibiotics known to inhibit the mitochondrial ribosome or mitochondrial protein translation as an off-target side-effect. These examples include chloramphenicol, actinonin, and levofloxacin. Each of these compounds may be chemically-modified with at least one mitochondria-targeting compound to form an antimitoscin. FIG. 4 shows other antibiotics known to impact mitochondrial oxygen consumption by interfering with mitochondrial complexes I, II, III, IV, and/or V. These examples include pyrvinium pamoate, atovaquone, and bedaquiline. Each of these compounds may be chemically-modified with at least one mitochondria-targeting compound to form an antimitoscin.

Figure 6B:
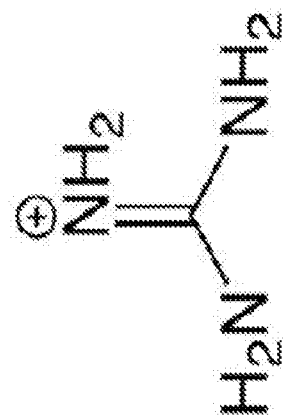
FIG. 6 shows the structures of mitochondria-targeting signals including (A) tri-phenyl-phosphonium (TPP) and (B) guanidinium.
Figure 6A:
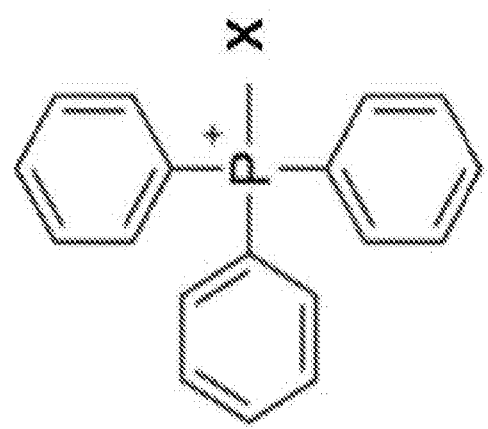

Unlike antibiotics, antimitoscins are specifically designed to target mitochondria by attachment of at least one membrane-targeting signal and/or at least one mitochondrial-targeting signal. FIG. 5 provides examples of membrane-targeting signals, including fatty acids such as palmitate, stearate, myristate, and oleate. It should be appreciated that this is not a comprehensive list of membrane-targeting signals, and that an unlisted membrane-targeting signal may be used without departing from the present approach. FIG. 6 provides examples of mitochondria-targeting signals, including tri-phenyl-phosphonium (TPP) and guanidinium-based moieties. It should be appreciated that this is not a comprehensive list of mitochondria-targeting signals, and that an unlisted mitochondria-targeting signal may be used without departing from the present approach.

Figure 7:
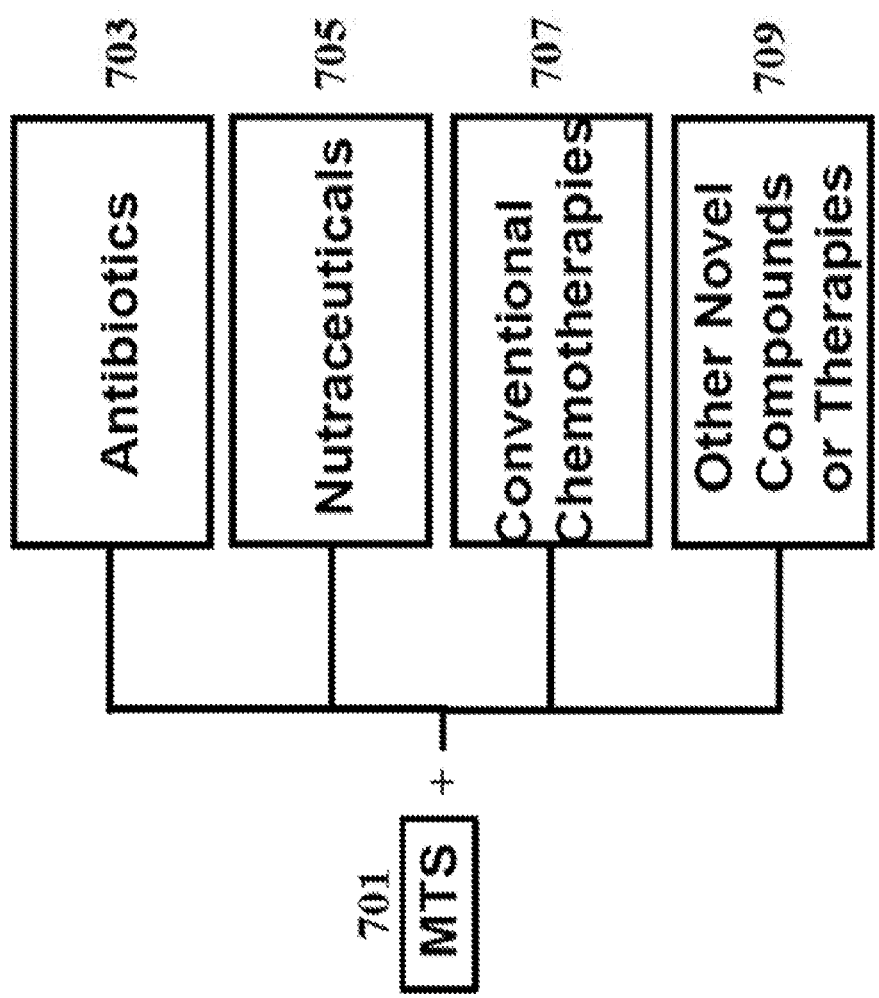
FIG. 7 shows a diagram of methods of converting antibiotics to antimitoscins by means of attachment (covalent or non-covalent) of a membrane or mitochondrial targeting signal to an antibiotic.

FIG. 7 shows a diagram of methods of converting antibiotics to antimitoscins by means of attachment (covalent or non-covalent) of a membrane or mitochondrial targeting signal 701 to one or more of antibiotics 703, nutraceuticals 705, conventional chemotherapies 707 as are known in the art, and other compounds or therapies 709.

Figure 8A:
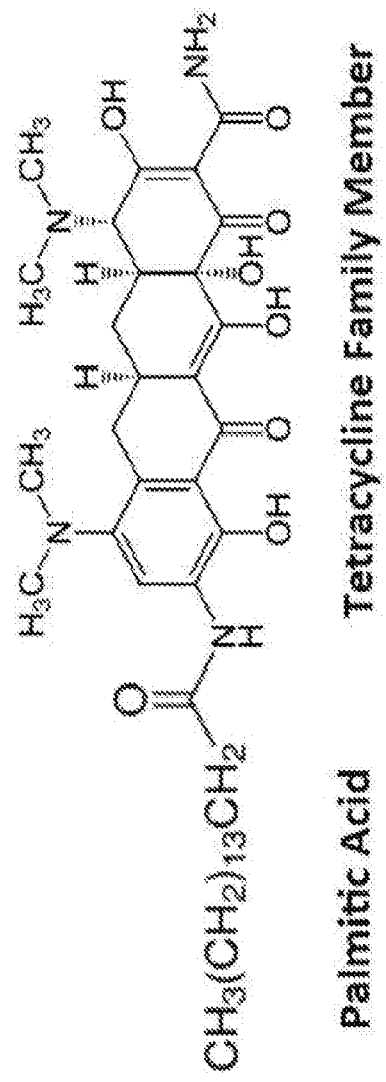
FIG. 8 shows the structures of two antimitoscins.
Figure 8B:
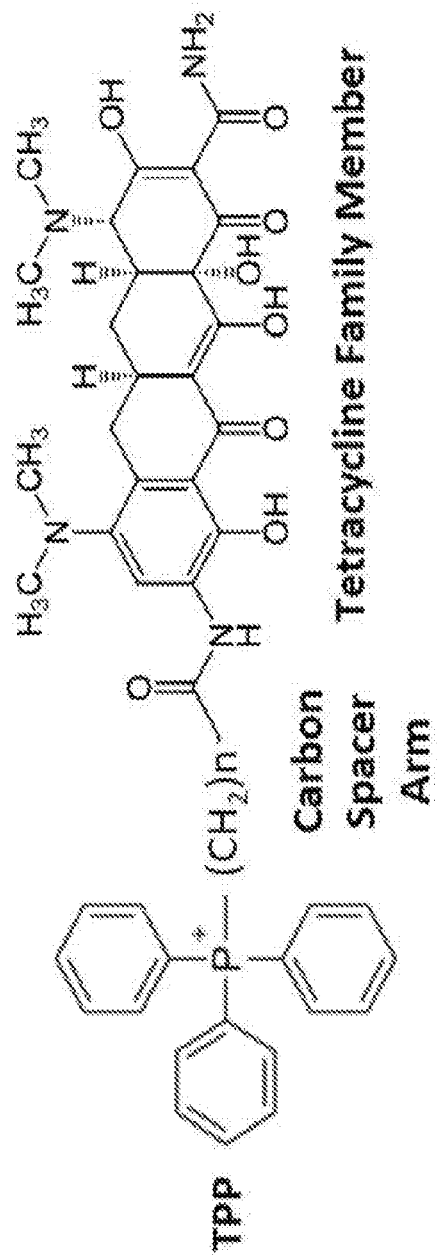

As described herein, an antimitoscin may be formed by chemically-modifying an antibiotic having intrinsic anti-mitochondrial properties with at least one membrane-targeting signal and/or at least one mitochondria-targeting signal. FIG. 8 shows two examples of antimitoscins. In these examples, the side chain of a tetracycline family member has been replaced with (A) palmitic acid and (B) a carbon-spacer-arm and TPP. It should be appreciated that the mitochondria-targeting compound(s) may be linked to the antibiotic in other locations without departing from the present approach.

The specific antimitoscin formulas shown in FIG. 8 are examples of antimitoscins formed from the exemplar antibiotics identified in FIGS. 1-4. It should be appreciated that an antimitoscin may be selected for therapeutic use individually, or in combination with one or more antimitoscin, and/or with other substances to enhance the efficacy of other therapeutics. For example, antimitoscins formed from different antibiotics may be used together in a therapeutic formulation. Further, antimitoscins formed from the antibiotic but having different mitochondria-targeting compounds (such as the structures shown in FIG. 8) may be used together in a therapeutic formulation. The therapeutics may be used in the form of usual pharmaceutical compositions which may be prepared using one or more known methods. For example, a pharmaceutical composition may be prepared by using diluents or excipients such as, for example, one or more fillers, bulking agents, binders, wetting agents, disintegrating agents, surface active agents, lubricants, and the like as are known in the art. Various types of administration unit forms can be selected depending on the therapeutic purpose(s). Examples of forms for pharmaceutical compositions include, but are not limited to, tablets, pills, powders, liquids, suspensions, emulsions, granules, capsules, suppositories, injection preparations (solutions and suspensions), topical creams, and other forms as may be known in the art. For the purpose of shaping a pharmaceutical composition in the form of tablets, any excipients which are known may be used, for example carriers such as lactose, white sugar, sodium chloride, glucose, urea, starch, calcium carbonate, kaolin, cyclodextrins, crystalline cellulose, silicic acid and the like; binders such as water, ethanol, propanol, simple syrup, glucose solutions, starch solutions, gelatin solutions, carboxymethyl cellulose, shelac, methyl cellulose, potassium phosphate, polyvinylpyrrolidone, etc. Additionally, disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, etc., may be used. Disintegration inhibitors such as white sugar, stearin, coconut butter, hydrogenated oils; absorption accelerators such as quaternary ammonium base, sodium laurylsulfate, etc., may be used. Wetting agents such as glycerin, starch, and others known in the art may be used. Adsorbing agents such as, for example, starch, lactose, kaolin, bentonite, colloidal silicic acid, etc., may be used. Lubricants such as purified talc, stearates, boric acid powder, polyethylene glycol, etc., may be used. If tablets are desired, they can be further coated with the usual coating materials to make the tablets as sugar coated tablets, gelatin film coated tablets, tablets coated with enteric coatings, tablets coated with films, double layered tablets, and multi-layered tablets. Pharmaceutical compositions adapted for topical administration may be formulated as ointments, creams, suspensions, lotions, powders, solutions, pastes, gels, foams, sprays, aerosols, or oils. Such pharmaceutical compositions may include conventional additives which include, but are not limited to, preservatives, solvents to assist drug penetration, co-solvents, emollients, propellants, viscosity modifying agents (gelling agents), surfactants, and carriers.

Antimitoscins may also be used to reverse drug resistance in cancer cells. Drug resistance is thought to be based, at least in part, on increased mitochondrial function in cancer cells. In particular, cancer cells demonstrating resistance to endocrine therapies, such as tamoxifen, are expected to have increased mitochondrial function. Antimitoscins inhibit mitochondrial function, and therefore are useful in reducing and, in some cases reversing, drug resistance in cancer cells. Additionally, previously generated data suggests that inhibitors of mitochondrial function that target the mitochondrial ribosome, referred to as "mitoriboscins," may be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances, such as dietary supplements and caloric restriction. Given their mitochondrial-inhibition properties, antimitoscins may similarly be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances.

In addition to antibiotics, other compounds having antibiotic activity may be modified with a membrane or mitochondria-targeting signal to have enhanced anti-cancer activity. For example, nutraceuticals and conventional chemotherapies may be modified with at least one mitochondria-targeting compound(s) to specifically target the mitochondria. The efficacy of such compounds may be increased when specifically targeting the mitochondria. Examples of nutraceuticals having antibiotic activity that may be modified to target the mitochondria include caffeic acid phenethyl ester (found in bee propolis), ascorbic acid (vitamin C) and other vitamins and trace minerals, polyphenols, epigallocatechin-3-gallate, resveratrol, and quercetin. It should be appreciated that this is not a comprehensive list of nutraceuticals having antibiotic activity, and that an unlisted nutraceutical may be used without departing from the present approach.

The table below summarizes demonstrative antibiotics and chemical targeting signals that may be linked to create an antimitoscin.

TABLE 1

Demonstrative constituents for creating an antimitoscin.

FDA-Approved Antibiotics

Tetracycline Family
tetracycline
minocycline
doxycycline
tigecycline
among others
Erythromycin Family
erythromycin
clarithromycin
azithromycin
among others
Other(s) & OXPHOS
chloramphenicol
pyrvinium pamoate
atovaquone
Bedaquiline
among others
Chemical Modifications Membrane-Targeting-Signals
palmitic acid
stearic acid
myristic acid
oleic acid
among others
Mitochondrial-Targeting-Signals
tri-phenyl-phosphonium (TPP)
guanidinium-related groups
choline esters
among others
Other Applications Nutraceuticals
Conventional chemotherapies
Newly Discovered Compounds
Specific Formulations Inert ingredients
Cyclodextrins
alpha
beta
Gamma
Combination
Therapies The present disclosure also relates to methods of monitoring the effectiveness of antimitoscin therapies. In some embodiments, one or more CSC markers may be monitored to determine the effectiveness of treatment with one or more antimitoscins. Relative levels of CSC markers may decrease in response to antimitoscin treatment, as compared to an untreated control. In some embodiments, the CSC marker is at least one of CD44, Sox2, Nanog, Oct4, MYC, and ALDH. The relative levels of one or more CSC markers may be measured in a tumor tissue sample. The relative levels of one or more CSC markers may be measured by any number of ways known in the art for measuring RNA, DNA, and/or protein levels of a marker including, without limitation, quantitative PCR and/or RT-PCR kits, microarrays, Northern blots, and Western blots.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed an element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method of treating cancer stem cells comprising administering to a patient in need thereof of a pharmaceutically effective amount of an antimitoscin and a pharmaceutically acceptable carrier, the antimitoscin comprising an antibiotic having intrinsic anti-mitochondrial properties and chemically modified with a membrane targeting signal comprising a fatty acid moiety, wherein the antibiotic is selected from the group consisting of tetracycline, doxycycline, tigecycline, minocycline, chlortetracycline, oxytetracycline, demeclocycline, lymecycline, meclocycline, methacycline, rolitetracycline, and sarecycline;
   wherein the fatty acid moiety consists of palmitic acid, stearic acid, myristic acid, or oleic acid; and
   the cancer stem cells are dependent on mitochondrial biogenesis.

2. The method of claim 1, wherein the antibiotic comprises doxycycline, and the fatty acid moiety is myristic acid.

3. The method of claim 1, wherein the antibiotic is one of doxycycline, tetracycline, and tigecycline.

4. The method of claim 1, wherein the fatty acid moiety is myristic acid.

5. The method of claim 1, wherein the antibiotic is one of doxycycline, tetracycline, and tigecycline, and wherein the fatty acid moiety is myristic acid.

6. The method of claim 1, wherein the antimitoscin comprises the formula:
, or pharmaceutically acceptable salts thereof.

* * * * *